US012805565B2

(12) United States Patent
Wright et al.

(10) Patent No.: US 12,805,565 B2
(45) **Date of Patent: *Nov. 24, 2026**

(54) ELECTRONIC AEROSOL PROVISION SYSTEM

(71) Applicant: NICOVENTURES TRADING LIMITED, London (GB)

(72) Inventors: Jeremy Wright, London (GB); Simon Rucker, Brentwood (GB)

(73) Assignee: NICOVENTURES TRADING LIMITED, London (GB)

( * ) Notice: Subject to any disclaimer, the term of this patent is extended or adjusted under 35 U.S.C. 154(b) by 0 days.

This patent is subject to a terminal disclaimer.

(21) Appl. No.: 18/798,091

(22) Filed: Aug. 8, 2024

(65) Prior Publication Data

US 2024/0398005 A1 Dec. 5, 2024

Related U.S. Application Data

(63) Continuation of application No. 16/758,218, filed as application No. PCT/GB2018/053052 on Oct. 23, 2018, now Pat. No. 12,161,155.

(30) Foreign Application Priority Data

Oct. 24, 2017 (GB) ..................................... 1717484

(51) Int. Cl.
*A24F 40/40* (2020.01)
*A24F 40/10* (2020.01)
(Continued)

(52) U.S. Cl.
CPC .............. *A24F 40/40* (2020.01); *A24F 40/51* (2020.01); *A24F 40/60* (2020.01); *A24F 40/70* (2020.01);
(Continued)

(58) Field of Classification Search
None
See application file for complete search history.

(56) References Cited

U.S. PATENT DOCUMENTS 2,005,557 A 6/1935 Penney
3,979,228 A 9/1976 Marchetti
(Continued)

FOREIGN PATENT DOCUMENTS

AU 2018356939 B2 7/2021
CN 1981651 A 6/2007
(Continued)

OTHER PUBLICATIONS

Japanese Patent Application No. 202267128, Notice of Reasons for Refusal, mailed May 28, 2025, 29 pages.
(Continued)

*Primary Examiner* — Phu H Nguyen
(74) *Attorney, Agent, or Firm* — MERCHANT & GOULD P.C.

(57) ABSTRACT

There is provided a device for an electronic aerosol provision system, wherein the device includes a housing, the housing being formed of a chassis section and a hatch section. The hatch section is connected to the chassis section and moveable between a first position wherein the chassis section and hatch section together define an enclosed space for an aerosol forming component to be located for aerosol generation, and a second position wherein the chassis section and hatch section are spaced so as to provide access to the space.

5 Claims, 12 Drawing Sheets

(51) Int. Cl.

| | |
|---|---|
| ***A24F 40/51*** | (2020.01) |
| ***A24F 40/60*** | (2020.01) |
| ***A24F 40/70*** | (2020.01) |
| ***A24F 40/95*** | (2020.01) |
| ***A61M 15/00*** | (2006.01) |

(52) U.S. Cl.

CPC ......... *A24F 40/95* (2020.01); *A61M 15/0021* (2014.02); *A61M 15/0028* (2013.01); *A24F 40/10* (2020.01)

(56) References Cited

U.S. PATENT DOCUMENTS

| | | | |
|---|---|---|---|
| 4,884,317 | A | 12/1989 | Liu |
| 5,048,515 | A | 9/1991 | Sanso |
| 6,065,626 | A | 5/2000 | Huang et al. |
| 6,135,106 | A | 10/2000 | Dirks et al. |
| 6,942,118 | B2 | 9/2005 | Zethoff et al. |
| 9,089,166 | B1 | 7/2015 | Scatterday |
| 9,320,299 | B2 | 4/2016 | Hearn et al. |
| D877,407 | S | 3/2020 | Wright et al. |
| D881,454 | S | 4/2020 | Wright et al. |
| D881,455 | S | 4/2020 | Wright et al. |
| D881,461 | S | 4/2020 | Wright et al. |
| D881,462 | S | 4/2020 | Wright et al. |
| D883,568 | S | 5/2020 | Wright et al. |
| D884,265 | S | 5/2020 | Wright et al. |
| 10,925,317 | B2 | 2/2021 | Smith et al. |
| 11,197,504 | B2 | 12/2021 | Lee |
| 11,925,205 | B2 | 3/2024 | Wright |
| 2005/0016550 | A1 | 1/2005 | Katase |
| 2007/0045288 | A1 | 3/2007 | Nelson |
| 2011/0180433 | A1 | 7/2011 | Rennecamp |
| 2012/0227753 | A1 | 9/2012 | Newton |
| 2012/0255546 | A1 | 10/2012 | Goetz et al. |
| 2012/0318283 | A1 | 12/2012 | Watanabe et al. |
| 2013/0037042 | A1 | 2/2013 | Hearn et al. |
| 2014/0014124 | A1 | 1/2014 | Glasberg et al. |
| 2015/0027459 | A1 | 1/2015 | Collett et al. |
| 2015/0128971 | A1 | 5/2015 | Verleur et al. |
| 2015/0164138 | A1 | 6/2015 | Liu |
| 2015/0245654 | A1 | 9/2015 | Memari et al. |
| 2015/0328415 | A1 | 11/2015 | Minskoff et al. |
| 2015/0342258 | A1 | 12/2015 | Chen |
| 2016/0050975 | A1 | 2/2016 | Worm et al. |
| 2016/0120222 | A1 | 5/2016 | Bagai et al. |
| 2016/0120226 | A1 | 5/2016 | Rado |
| 2016/0120266 | A1 | 5/2016 | Huang |
| 2016/0150824 | A1 | 6/2016 | Memari et al. |
| 2016/0338412 | A1 | 11/2016 | Monsees et al. |
| 2016/0374401 | A1 | 12/2016 | Liu |
| 2017/0027221 | A1 | 2/2017 | Liu |
| 2017/0064997 | A1 | 3/2017 | Murison et al. |
| 2017/0095623 | A1 | 4/2017 | Trzecieski |
| 2017/0099878 | A1 | 4/2017 | Murison et al. |
| 2017/0143038 | A1 | 5/2017 | Dickens |
| 2017/0156403 | A1 | 6/2017 | Gill et al. |
| 2017/0172211 | A1 | 6/2017 | Batista et al. |
| 2017/0181471 | A1 | 6/2017 | Phillips et al. |
| 2017/0222468 | A1 | 8/2017 | Schennum et al. |
| 2017/0273355 | A1 | 9/2017 | Rogers et al. |
| 2019/0098930 | A1 | 4/2019 | Fallon et al. |
| 2019/0150516 | A1 | 5/2019 | Shenkal et al. |
| 2019/0254344 | A1 | 8/2019 | Hepworth et al. |
| 2019/0254346 | A1 | 8/2019 | Hepworth et al. |
| 2020/0281264 | A1 | 9/2020 | Wright |
| 2020/0281267 | A1 | 9/2020 | Wright |
| 2020/0281268 | A1 | 9/2020 | Wright |
| 2020/0288775 | A1 | 9/2020 | Wright et al. |
| 2020/0288776 | A1 | 9/2020 | Wright |
| 2020/0323266 | A1 | 10/2020 | Wright et al. |

FOREIGN PATENT DOCUMENTS

| | | | |
|---|---|---|---|
| CN | 201451347 | U | 5/2010 |
| CN | 101862038 | A | 10/2010 |
| CN | 102406238 | A | 4/2012 |
| CN | 102811634 | A | 12/2012 |
| CN | 103202537 | A | 7/2013 |
| CN | 103689812 | A | 4/2014 |
| CN | 203692551 | U | 7/2014 |
| CN | 203789158 | U | 8/2014 |
| CN | 104095293 | A | 10/2014 |
| CN | 104582772 | A | 4/2015 |
| CN | 204317504 | U | 5/2015 |
| CN | 104770896 | A | 7/2015 |
| CN | 204466899 | U | 7/2015 |
| CN | 105188429 | A | 12/2015 |
| CN | 105658099 | A | 6/2016 |
| CN | 205337606 | U | 6/2016 |
| CN | 105852225 | A | 8/2016 |
| CN | 105939625 | A | 9/2016 |
| CN | 106170218 | A | 11/2016 |
| CN | 106455725 | A | 2/2017 |
| CN | 106509991 | A | 3/2017 |
| CN | 106572708 | A | 4/2017 |
| CN | 106686997 | A | 5/2017 |
| CN | 106880086 | A | 6/2017 |
| CN | 106998815 | A | 8/2017 |
| CN | 109640712 | A | 4/2019 |
| EP | 845200 | A1 | 6/1998 |
| EP | 970627 | A1 | 1/2000 |
| EP | 2875740 | A2 | 5/2015 |
| EP | 3132698 | A1 | 2/2017 |
| EP | 3167728 | A1 | 5/2017 |
| EP | 3199043 | A1 | 8/2017 |
| EP | 3381305 | A1 | 10/2018 |
| EP | 3530128 | A1 | 8/2019 |
| GB | 354564 | A | 8/1931 |
| GB | 2514893 | A | 12/2014 |
| GB | 2523585 | A | 9/2015 |
| GB | 2534209 | A | 7/2016 |
| GB | 2542017 | A | 3/2017 |
| JP | S51138824 | A | 11/1976 |
| JP | H0879342 | A | 3/1996 |
| JP | 2001044659 | A | 2/2001 |
| JP | 2006032441 | A | 2/2006 |
| JP | 2006156322 | A | 6/2006 |
| JP | 2007165723 | A | 6/2007 |
| JP | 2012135299 | A | 7/2012 |
| JP | 2012529898 | A | 11/2012 |
| JP | 2013518577 | A | 5/2013 |
| JP | 2015503335 | A | 2/2015 |
| JP | 2015504668 | A | 2/2015 |
| JP | 2015529458 | A | 10/2015 |
| JP | 2016521552 | A | 7/2016 |
| JP | 2016169049 | A | 9/2016 |
| JP | 2017501805 | A | 1/2017 |
| JP | 2017506890 | A | 3/2017 |
| JP | 2017506915 | A | 3/2017 |
| JP | 2017513513 | A | 6/2017 |
| JP | 2017522293 | A | 8/2017 |
| JP | 2017523093 | A | 8/2017 |
| JP | 2019503676 | A | 2/2019 |
| JP | 2019513349 | A | 5/2019 |
| JP | 2019532638 | A | 11/2019 |
| KR | 20120114333 | A | 10/2012 |
| KR | 20170088106 | A | 8/2017 |
| RU | 2183418 | C2 | 6/2002 |
| RU | 2510711 | C1 | 4/2014 |
| RU | 2536032 | C2 | 12/2014 |
| RU | 2602964 | C2 | 11/2016 |
| RU | 2604480 | C2 | 12/2016 |
| WO | 9748293 | A1 | 12/1997 |
| WO | 2011095781 | A1 | 8/2011 |
| WO | 2013156339 | A1 | 10/2013 |
| WO | 2014066730 | A1 | 5/2014 |
| WO | 2015061966 | A1 | 5/2015 |
| WO | 2015117700 | A1 | 8/2015 |
| WO | 2015157891 | A1 | 10/2015 |
| WO | 2015177046 | A1 | 11/2015 |

(56) References Cited

FOREIGN PATENT DOCUMENTS

| | | | |
|---|---|---|---|
| WO | 2015198051 | A1 | 12/2015 |
| WO | 2016026811 | A1 | 2/2016 |
| WO | 2016054580 | A1 | 4/2016 |
| WO | 2016075028 | A1 | 5/2016 |
| WO | 2016079152 | A1 | 5/2016 |
| WO | 2016111633 | A1 | 7/2016 |
| WO | 2016162446 | A1 | 10/2016 |
| WO | 2017037457 | A1 | 3/2017 |
| WO | 2017093452 | A1 | 6/2017 |
| WO | 2017102633 | A1 | 6/2017 |
| WO | 2017167932 | A1 | 10/2017 |

OTHER PUBLICATIONS

Decision of Dismissal of Amendment received for Japanese Patent Application No. 2022-067128, mailed on Oct. 3, 2023, 8 pages.

Decision to Grant received for Japanese Patent Application No. 2020-522854, mailed on Apr. 19, 2022, 5 pages.

Decision to Grant received for Japanese Patent Application No. 2022-082164, mailed on Oct. 3, 2023, 5 pages.

Examination Report received for Australian Patent Application No. 2018356939, mailed on Feb. 23, 2021, 6 Pages.

Examination Report received for Australian Patent Application No. 2018356942, mailed on Apr. 13, 2021, 5 pages.

International Preliminary Report on Patentability received for PCT Patent Application No. PCT/GB2018/053026, mailed on Jan. 29, 2020, 6 pages.

International Preliminary Report on Patentability received for PCT Patent Application No. PCT/GB2018/053027, mailed on May 7, 2020, 11 pages.

International Preliminary Report on Patentability received for PCT Patent Application No. PCT/GB2018/053028, mailed on May 7, 2020, 9 pages.

International Preliminary Report on Patentability received for PCT Patent Application No. PCT/GB2018/053029, mailed on Jan. 30, 2020, 8 pages.

International Preliminary Report on Patentability received for PCT Patent Application No. PCT/GB2018/053030, mailed on May 7, 2020, 10 pages.

International Preliminary Report on Patentability received for PCT Patent Application No. PCT/GB2018/053052, mailed on Jan. 29, 2020, 13 pages.

International Search Report and Written Opinion received for PCT Patent Application No. PCT/GB2018/053030, mailed on Mar. 22, 2019, 19 Pages.

International Search Report and Written Opinion received for PCT Patent Application No. PCT/GB2018/053029, mailed on Jan. 28, 2019, 13 pages.

International Search Report and Written Opinion received for PCT Patent Application No. PCT/GB2018/053026, mailed on Jan. 21, 2019, 9 pages.

International Search Report and Written Opinion received for PCT Patent Application No. PCT/GB2018/053027, mailed on Mar. 20, 2019, 20 pages.

International Search Report and Written Opinion received for PCT Patent Application No. PCT/GB2018/053028, mailed on Jan. 28, 2019, 15 pages.

International Search Report and Written Opinion received for PCT Patent Application No. PCT/GB2018/053052, mailed on Jan. 21, 2019, 13 pages.

Invitation to Pay Additional Fees received for PCT Patent Application No. PCT/GB2018/053027, mailed on Jan. 25, 2019, 13 pages.

Invitation to Pay Additional Fees/Partial International Search Report received for PCT Patent Application No. PCT/GB2018/053030, mailed Jan. 30, 2019, 17 Pages.

Notice of Reasons for Rejection received for Japanese Patent Application No. 2022-067128, mailed on Jun. 6, 2023, 9 pages.

Office Action received for Canadian Application No. 3,084,454, mailed on Aug. 30, 2021, 5 Pages.

Office Action received for Chinese Patent Application No. 201880068679.4, mailed on Jul. 22, 2022, 17 pages.

Office Action received for Chinese Patent Application No. 201880069204.7, mailed on Jul. 27, 2022, 17 pages.

Office Action received for Chinese Patent Application No. 201880069227.8, mailed on Jul. 15, 2022, 18 pages.

Office Action received for Chinese Patent Application No. 201880069227.8, mailed on Jun. 1, 2023, 15 pages.

Office Action received for Chinese Patent Application No. 201880069242.2, mailed on Apr. 25, 2023, 25 pages.

Office Action received for Chinese Patent Application No. 201880069242.2, mailed on Jul. 27, 2022, 18 pages.

Office Action received for European Patent Application No. 18795771.7, mailed on Apr. 25, 2024, 20 pages.

Office Action received for Korean Patent Application No. 10-2020-7011679, mailed Dec. 20, 2021, 23 pages.

Office Action received for Russian Application No. 2020114426, mailed on Feb. 3, 2021, 9 pages.

Office Action received for Russian Patent Application No. 2021106972, mailed on Apr. 11, 2022, 7 pages.

"Polymer filtration media", Bekipor® ST, available at https://www.bekaert.com/en/products/basic-materials/filtration/ polymer-filtration-media, 2023, 4 pages.

Reason for Refusal received for Japanese Application No. 2020-522816 mailed Jun. 22, 2021, 12 pages.

Reason for Refusal received for Japanese Application No. 2020-522816 mailed Sep. 13, 2022, 35 pages.

Reason for Refusal received for Japanese Patent Application No. 2020-522893, mailed on Jul. 6, 2021, 12 pages.

Reason for Refusal received for Japanese Patent Application No. 2020-522988, mailed Aug. 3, 2021, 10 pages.

Reason for Refusal received for Japanese Patent Application No. 2022-082164, mailed on Apr. 4, 2023, 8 pages.

Search Report received for Great Britain Patent Application No. 1717479.8 mailed on Apr. 25, 2018, 6 Pages.

Search Report received for Great Britain Patent Application No. 1717480.6, mailed on Apr. 24, 2018, 3 pages.

Search Report received for Great Britain Patent Application No. 1717484.8, mailed on Apr. 24, 2018, 4 pages.

Search Report received for Great Britain Patent Application No. 1717486.3, mailed on Apr. 25, 2018, 4 pages.

Search Report received for Great Britain Patent Application No. 1717489.7, mailed on Apr. 23, 2018, 3 pages.

Search Report received for Japanese Patent Application No. 2020-522816, mailed on Jun. 16, 2021, 19 pages.

Search Report received for Japanese Patent Application No. 2020-522988, mailed on Jul. 21, 2021, 19 pages.

Search Report received for Russian Patent Application No. 2020114244 mailed on Nov. 17, 2020, 3 pages.

Search Report received for Russian Patent Application No. 2020114320, mailed on Dec. 21, 2020, 2 pages.

Search Report received for Russian Patent Application No. 2020114326 mailed on Oct. 14, 2020, 2 pages.

Search Report received for Russian Patent Application No. 2020114395 mailed on Sep. 11, 2020, 2 pages.

Written Opinion of the International Preliminary Examining Authority received for PCT Patent Application No. PCT/GB2018/053029, mailed on Oct. 17, 2019, 7 pages.

Written Opinion of the International Preliminary Examining Authority received for PCT Patent Application No. PCT/GB2018/053026, mailed on Oct. 4, 2019, 6 pages.

Toulas, Bill , "AISI 304 Stainless Steel: Specification and Datasheet", available at available at https://www.engineeringclicks.com/aisi-304-stainless-steel/, Dec. 13, 2018, 11 pages.

Toulas, Bill, "AISI 316 Stainless Steel: Specification and Datasheet", available at available at https://www.engineeringclicks.com/aisi-316-stainless-steel/, Nov. 1, 2018, 11 pages.

Wright, et al., "Application and File History for U.S. Appl. No. 16/758,218, filed Apr. 22, 2020".

Wright, "Application and File History for U.S. Appl. No. 16/758,222, filed Apr. 22, 2020".

(56) References Cited

OTHER PUBLICATIONS

Wright, "Application and File History for U.S. Appl. No. 16/758,225, filed Apr. 22, 2020".
Wright, "Application and File History for U.S. Appl. No. 16/758,226, filed Apr. 22, 2020".
Wright, "Application and File History for U.S. Appl. No. 16/758,229, filed Apr. 22, 2020".

ELECTRONIC AEROSOL PROVISION SYSTEM

PRIORITY CLAIM

The present application is a continuation application of U.S. application Ser. No. 16/758,218 filed Apr. 22, 2020, which is a National Phase entry of PCT Application No. PCT/GB2018/053052, filed Oct. 23, 2018, which claims priority from GB Patent Application No. 1717484.8, filed Oct. 24, 2017, each of which is hereby fully incorporated herein by reference.

FIELD

The present disclosure relates to electronic aerosol provision systems such as nicotine delivery systems (e.g. electronic cigarettes and the like).

BACKGROUND

Electronic aerosol provision systems such as electronic cigarettes (e-cigarettes) generally contain a device section containing a power source and possibly electronics for operating the device, and an aerosol provision component which may comprise a reservoir of a source material, such as a liquid, containing a formulation, typically including nicotine, from which an aerosol is generated, e.g. through heat vaporization. An aerosol provision component for an aerosol provision system may thus comprise a heater having a heating element arranged to receive source material from the reservoir, for example through wicking/capillary action.

While a user inhales on the system, electrical power is supplied from the device section to the heating element in the aerosol provision component to vaporize source material in the vicinity of the heating element to generate an aerosol for inhalation by the user. Such systems are usually provided with one or more air inlet holes located away from a mouthpiece end of the system. When a user sucks on a mouthpiece connected to the mouthpiece end of the system, air is drawn in through the inlet holes and past/through the aerosol provision component. There is a flow path connecting between the aerosol provision component and an opening in the mouthpiece so that air drawn past the aerosol provision component continues along the flow path to the mouthpiece opening, carrying some of the aerosol from the aerosol provision component with it. The aerosol-carrying air exits the aerosol provision system through the mouthpiece opening for inhalation by the user.

Electronic cigarettes will include a mechanism for activating the heater to vaporize the source material during use. One approach is to provide a manual activation mechanism, such as a button, which the user presses to activate the heater. In such devices, the heater may be activated (i.e. supplied with electrical power) while the user is pressing the button, and deactivated when the user releases the button. Another approach is to provide an automatic activation mechanism, such as a pressure sensor arranged to detect when a user is drawing air through the system by inhaling on the mouthpiece. In such systems, the heater may be activated when it is detected the user is inhaling through the device and deactivated when it is detected the user has stopped inhaling through the device.

Typically, three types of electronic aerosol provision systems have been provided to date. Firstly, devices are known where the aerosol provision component and the power containing device section are inseparable and contained within the same housing. Secondly, devices are known where the aerosol provision component and the power containing device section are separable. Such devices facilitate re-use of the device section (via recharging of the power source, for example). Thirdly, devices are known where the aerosol provision component and the power containing device section are separable, and the aerosol provision component itself may be further separated into component parts. For example, in some devices it is possible for the heater of the aerosol provision component to be removed from the aerosol provision component and replaced.

Typically, each of these devices are arranged in a generally longitudinal format. That is to say, the various component parts, e.g. the aerosol provision component and the device are generally attached in a sequential end-on format. To date, this has been acceptable to some users of such systems since they may resemble conventional combustible products such as cigarettes.

One consideration relating to such devices is that secure attachment between the aerosol provision component and the power section is required. To date, this has typically been achieved via screw-threads or other connections such as bayonet-fittings, or push-fittings.

A further consideration relating to such devices is the relatively exposed profile of the aerosol provision component. Since it generally extends from the device section, it might be considered as extending the overall profile of the device, which may be undesirable to some consumers.

Various approaches are described which seek to help address some of these issues.

SUMMARY

In accordance with some embodiments described herein, there is provided a device for an electronic aerosol provision system, wherein the device comprises a housing, said housing being formed of a chassis section and a hatch section, wherein the hatch section is connected to the chassis section and moveable between a first position where the chassis section and hatch section together define an enclosed space for an aerosol forming component to be located for aerosol generation, and a second position wherein the chassis section and hatch section are spaced so as to provide access to the space.

In accordance with some embodiments described herein, there is also provided an aerosol delivery system comprising: a device for an electronic aerosol provision system, wherein the device comprises a housing, said housing being formed of a chassis section and a hatch section, wherein the hatch section is connected to the chassis section and moveable between a first position where the chassis section and hatch section together define an enclosed space for an aerosol forming component to be located for aerosol generation, and a second position wherein the chassis section and hatch section are spaced so as to provide access to the space, a power supply, an activation means, electronics for operating the device, and an aerosol forming component.

In accordance with some embodiments described herein, there is also provided a process for manufacturing a device for an electronic aerosol provision system, wherein the device comprises a housing, said housing being formed of a chassis section and a hatch section, wherein the hatch section is connected to the chassis section and moveable between a first position where the chassis section and hatch section together define an enclosed space for an aerosol forming component to be located for aerosol generation, and a second position wherein the chassis section and hatch section are spaced so as to provide access to the space, the method comprising: forming the chassis section; forming the hatch section; connecting the chassis section to the hatch section.

BRIEF DESCRIPTION OF THE DRAWINGS

Embodiments of the disclosure will now be described, by way of example only, with reference to the accompanying drawings, in which.

DETAILED DESCRIPTION

Aspects and features of certain examples and embodiments are discussed/described herein. Some aspects and features of certain examples and embodiments may be implemented conventionally and these are not discussed/described in detail in the interests of brevity. It will thus be appreciated that aspects and features of apparatus and methods discussed herein which are not described in detail may be implemented in accordance with any conventional techniques for implementing such aspects and features.

As described above, the present disclosure relates to an aerosol provision system, such as an e-cigarette. Throughout the following description the term "e-cigarette" is sometimes used but this term may be used interchangeably with aerosol (vapor) provision system. Furthermore, an aerosol provision system may include systems which are intended to generate aerosols from liquid source materials, solid source materials and/or semi-solid source materials, e.g. gels. Certain embodiments of the disclosure are described herein in connection with some example e-cigarette configurations (e.g. in terms of a specific overall appearance and underlying vapor generation technology). However, it will be appreciated the same principles can equally be applied for aerosol delivery systems having different overall configurations (e.g. having a different overall appearance, structure and/or vapor generation technology).

Figure 1:
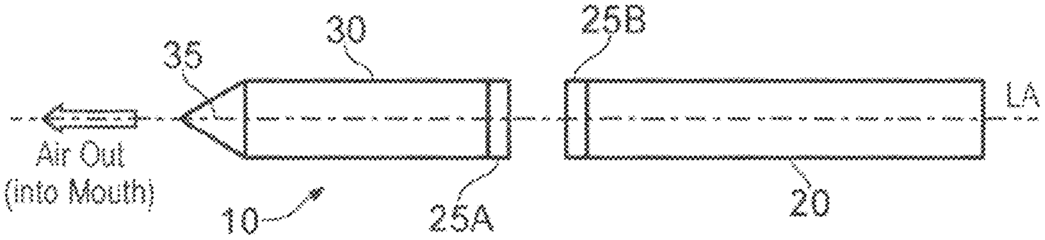
FIG. 1 is a schematic diagram of an electronic aerosol provision system such as an e-cigarette in accordance with some examples of the prior art.

FIG. 1 is a schematic diagram of an aerosol/vapor provision system of the prior art (not to scale). The e-cigarette 10 of the prior art has a generally cylindrical shape, extending along a longitudinal axis indicated by dashed line LA, and comprising two main components, namely a body 20 (device section) and a cartomizer 30 (aerosol provision component). The cartomizer includes an internal chamber containing a reservoir of a source liquid comprising a liquid formulation from which an aerosol is to be generated, a heating element, and a liquid transport element (in this example a wicking element) for transporting source liquid to the vicinity of the heating element. In some example implementations of an aerosol provision component according to embodiments of the present disclosure, the heating element may itself provide the liquid transport function. For example, the heating element and the element providing the liquid transport function may sometimes be collectively referred to as an aerosol generator/aerosol forming member/vaporizer/atomizer/distiller. The cartomizer 30 further includes a mouthpiece 35 having an opening through which a user may inhale the aerosol from the aerosol generator. The source liquid may be of a conventional kind used in e-cigarettes, for example comprising 0 to 5% nicotine dissolved in a solvent comprising glycerol, water, and/or propylene glycol. The source liquid may also comprise flavorings. The reservoir for the source liquid may comprise a porous matrix or any other structure within a housing for retaining the source liquid until such time that it is required to be delivered to the aerosol generator/vaporizer. In some examples the reservoir may comprise a housing defining a chamber containing free liquid (i.e. there may not be a porous matrix).

As discussed further below, the body 20 includes a re-chargeable cell or battery to provide power for the e-cigarette 10 and a circuit board including control circuitry for generally controlling the e-cigarette. In active use, i.e. when the heating element receives power from the battery, as controlled by the control circuitry, the heating element vaporizes source liquid in the vicinity of the heating element to generate an aerosol. The aerosol is inhaled by a user through the opening in the mouthpiece. During user inhalation the aerosol is carried from the aerosol source to the mouthpiece opening along an air channel that connects between them.

In the examples of the prior art, the body 20 and cartomizer 30 are detachable from one another by separating in a direction parallel to the longitudinal axis LA, as shown in FIG. 1, but are joined together when the device 10 is in use by a connection, indicated schematically in FIG. 1 as 25A and 25B, to provide mechanical and electrical connectivity between the body 20 and the cartomizer 30. The electrical connector on the body 20 that is used to connect to the cartomizer also serves as a socket for connecting a charging device (not shown) when the body is detached from the cartomizer 30. The other end of the charging device can be plugged into an external power supply, for example a USB socket, to charge or to re-charge the cell/battery in the body 20 of the e-cigarette. In other implementations, a cable may be provided for direct connection between the electrical connector on the body and the external power supply and/or the device may be provided with a separate charging port, for example a port conforming to one of the USB formats.

The e-cigarette 10 is provided with one or more holes (not shown in FIG. 1) for air inlet. These holes connect to an air passage (airflow path) running through the e-cigarette 10 to the mouthpiece 35. The air passage includes a region around the aerosol source and a section comprising an air channel connecting from the aerosol source to the opening in the mouthpiece.

When a user inhales through the mouthpiece 35, air is drawn into this air passage through the one or more air inlet holes, which are suitably located on the outside of the e-cigarette. This airflow (or the associated change in pressure) is detected by an airflow sensor 215, in this case a pressure sensor, for detecting airflow in electronic cigarette 10 and outputting corresponding airflow detection signals to the control circuitry. The airflow sensor 560 may operate in accordance with conventional techniques in terms of how it is arranged within the electronic cigarette to generate airflow detection signals indicating when there is a flow of air through the electronic cigarette (e.g. when a user inhales or blows on the mouthpiece).

When a user inhales (sucks/puffs) on the mouthpiece in use, the airflow passes through the air passage (airflow path) through the electronic cigarette and combines/mixes with the vapor in the region around the aerosol source to generate the aerosol. The resulting combination of airflow and vapor continues along the airflow path connecting from the aerosol source to the mouthpiece for inhalation by a user. The cartomizer 30 may be detached from the body 20 and disposed of when the supply of source liquid is exhausted (and replaced with another cartomizer if so desired). Alternatively, the cartomizer may be refillable.

In accordance with some example embodiments of the present disclosure, whilst the operation of the aerosol provision system may function broadly in line with that described above for exemplary prior art devices, e.g. activation of a heater to vaporize a source material so as to entrain an aerosol in a passing airflow which is then inhaled, the construction of the aerosol provision system of some example embodiments of the present disclosure is different to prior art devices.

Figure 2:
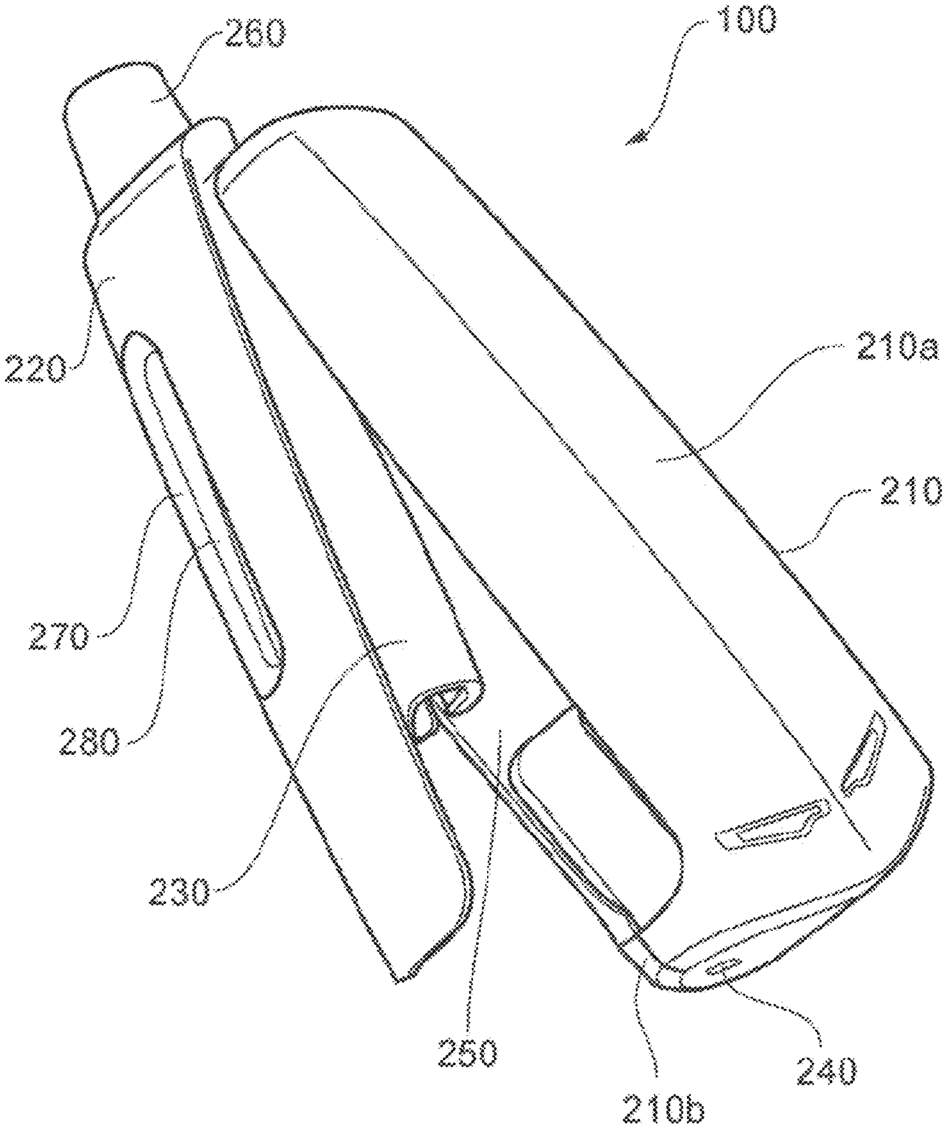
FIG. 2 is a diagram of a device in accordance with one embodiment of the present disclosure.
Figure 3:
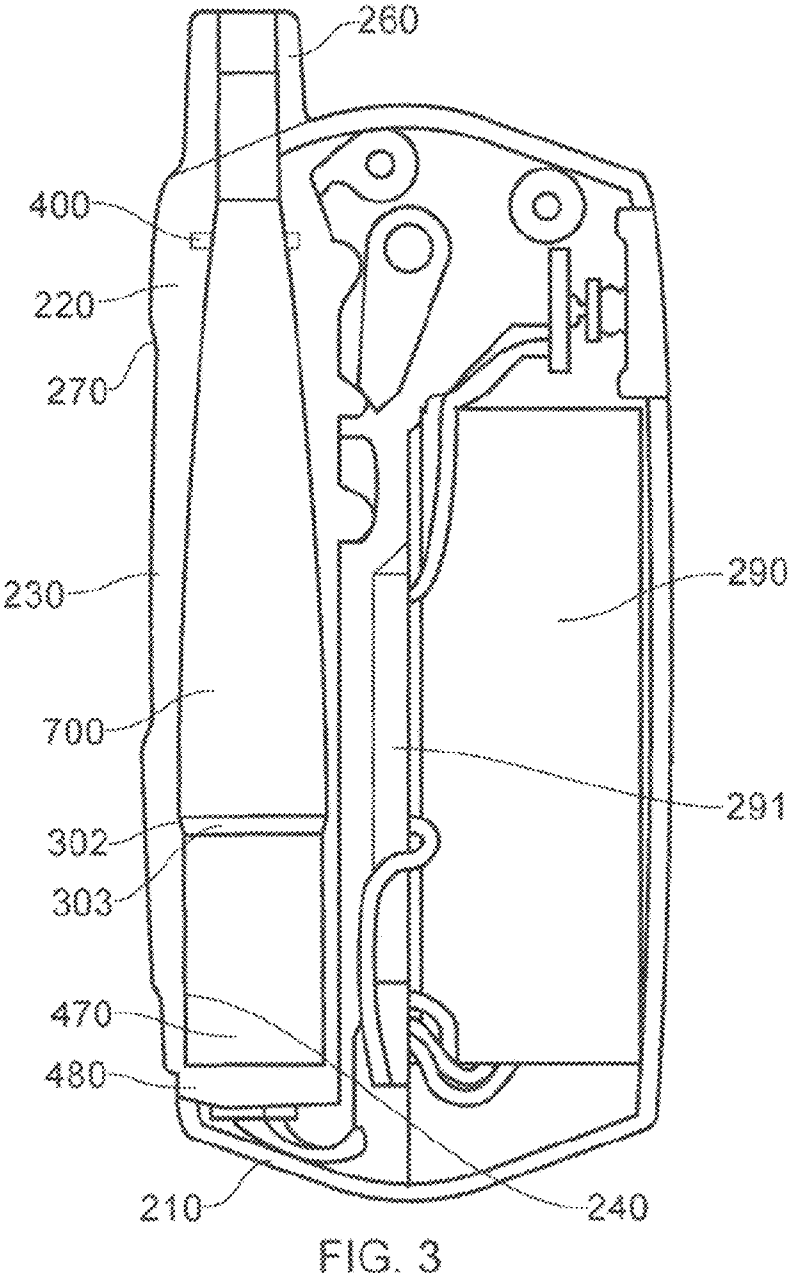
FIG. 3 is a cross sectional diagram of the device of FIG. 2 when the hatch section is in the first position and an aerosol forming component resides within the housing.

In this regard, a device for an electronic aerosol provision system is provided, wherein the device comprises a housing, said housing being formed of a chassis section and a hatch section, wherein the hatch section is connected to the chassis section and moveable between a first position where the chassis section and hatch section together define an enclosed space for an aerosol forming component to be located for aerosol generation, and a second position wherein the chassis section and hatch section are spaced so as to provide access to the space. FIG. 2 is a diagram of an exemplary device 100 according to one embodiment of the present disclosure. Note that various components and details of the body, e.g. such as wiring and more complex shaping, have been omitted from FIG. 2 for reasons of clarity. Some of these are shown in FIG. 3. Device 100 comprises a housing 200 formed by chassis section 210 and hatch section 220. Chassis section 210 may take the form of a single piece of material, or may be formed from two separate pieces of material 210*a*, 210*b* joined together along an appropriate seam (not shown). Chassis section 210 and hatch section 220 are connected such that hatch section 220 is moveable relative to the chassis section 210 between a first position where the chassis section 210 and hatch section 220 together define an enclosed space 250 for an aerosol forming component (not shown) to be located for aerosol generation, and a second position wherein the chassis section 210 and hatch section 220 are spaced so as to provide access to the space 250. FIG. 2 shows chassis section 210 and hatch section 220 in the second position with space 250 being accessible. As can also be seen in FIG. 2, in some embodiments, the hatch section 220 may comprise a sleeve 230 mounted on an internal wall of the hatch section 220 such that the sleeve projects towards the space 250. Sleeve 230 defines a generally longitudinal recess which is able to accommodate an aerosol forming component (not shown). More specifically, an aerosol forming component can be inserted into sleeve 230. Sleeve 230 will be explained in further detail below; however, in the context of the embodiment of FIG. 2, it will be apparent than when the hatch section 220 is moved to the first position such that, together with the chassis section 210, an enclosed space 250 is formed, the sleeve 230 (and the aerosol forming component if present) will occupy the space 250. Accordingly, by providing a hatch section which is moveable between first and second positions as described herein, it is possible to provide a space for an aerosol forming component to be received without otherwise extending the overall profile of the device. This can be advantageous for a number of reasons. Firstly, a more compact device is provided relative to the conventional longitudinal devices of the art. Secondly, the aerosol forming component is generally more protected than the in the devices of the prior art since it may be located entirely within an enclosed space, thus providing a degree of protection against impact from external objects. This can be particularly important given the presence of source liquid which could leak if the aerosol forming component is damaged.

The hatch section 220 of the device 100 shown in FIG. 2 may also comprise a mouthpiece 260 which defines an outlet. Additionally, the device 100 generally includes an inlet 240 which facilitates the inlet of air into the space 250. The inlet 240, space 250 and outlet 260 together form a fluidly connected pathway for air to flow from outside the device, through the space 250, and out of the outlet of the mouthpiece. When an aerosol forming component is present in the space 250, the air flow will be channeled through (or past) the aerosol forming component thereby facilitating the entrainment of aerosol in the airflow path.

As generally described herein, the device according to some example embodiments of the present disclosure may include a number of additional features. In one embodiment, the hatch section is an elongate component comprising an externally facing surface and an internally facing surface. In one embodiment, the hatch section includes a sleeve as part of the internally facing surface, wherein the sleeve is for receiving the aerosol forming component. In one embodiment, the sleeve has a generally tubular profile.

As explained herein, the hatch section is moveably connected to the chassis section. In one embodiment, moving the hatch section from the first position to the second position includes the hatch section undergoing at least one of pivoting, rotating, sliding, swiveling with respect to the chassis housing. Optionally, moving the hatch section from the first position to the second position includes the hatch section undergoing more than one of pivoting, sliding, swiveling with respect to the chassis housing. Optionally, moving the hatch section from the first position to the second position includes the hatch section undergoing sliding and pivoting with respect to the chassis housing, and in some embodiments, undergoing sliding and then pivoting with respect to the chassis housing.

The housing of the present device generally comprises one or more inlets for conveying air into the space when the hatch section is in the first position. The position of the inlet(s) is not particularly limited. For example, in one embodiment, at least one inlet is present on the hatch section. Additionally and/or alternatively, the at least one inlet is present on the chassis section. It may be desirable for the one or more inlets to be aligned with an air inlet on the aerosol forming component.

As explained above with respect to devices of the prior art, the device 100 of some example embodiments of the present disclosure can be activated by any suitable means. Such suitable activation means include button activation, or activation via a sensor (touch sensor, airflow sensor, pressure sensor, thermistor etc.). By activation, it is meant that the aerosol generator of the aerosol forming component can be energized such that vapor is produced from the source material. In this regard, activation can be considered to be distinct from actuation, whereby the device 100 is brought from an essentially dormant or off state, to a state in which once or more functions can be performed on the device and/or the device can be placed into a mode which can be suitable for activation.

In this regard, housing 200 generally comprises a power supply/source (not shown in FIG. 2) which supplies power to the aerosol generator of the aerosol forming component. It is noted that the connection between the aerosol forming component and the power supply may be wired or wireless. For example, where the connection is a wired connection, contacts 450 within the housing 200, for example on the chassis section 210, may contact with corresponding electrodes of the aerosol forming component when the hatch section 220 is in the first position and the aerosol forming component thus resides within space 250. The establishment of such contact will be explained further below. Alternatively, it is possible for the connection between the power source and the aerosol forming component to be wireless in the sense that a drive coil (not shown) present in the housing 200 and connected to the power source could be energized such that a magnetic field is produced. The aerosol forming component could then comprise a susceptor which is penetrated by the magnetic field such that eddy currents are induced in the susceptor and it is heated.

In an optional aspect of the device 100 of FIG. 2, there may be provided a surface feature 270 which facilitates movement of the hatch section 220 from the first position to the second position. The surface feature 270 will be explained in more detail below. In the context of the device 100 shown in FIG. 2, the surface feature 270 is a recess formed in the outer surface of hatch section 220. However, it will be understood that the surface feature may not be a recess, and could inserted be a projection, or area of increased surface roughness. In the context of the surface feature 270, there is provided an area for improved engagement with a digit of a user (such as a thumb) and therefore the movement of the hatch section 220 is improved since the thumb can, for example, reside in the recess and more easily move the hatch section 220 to the second position. The recessed surface feature 270 may in this case also define a transparent section 280 of hatch section 220. Such a transparent section allows the user to visualize the aerosol forming component, which could be advantageous in allowing the user to see information displayed on the aerosol forming component (such as flavor, brand, purchase date information etc.) and/or the amount of source material present in the aerosol forming component. Such transparent sections are generally not required on devices of the prior art since the aerosol forming component is generally fully exposed in a longitudinal type configuration. The transparent section may be located within the recess.

FIG. 3 provides a cross-sectional view of the device 100 of FIG. 2 wherein the hatch section 220 is in the first position and an aerosol forming component 700 is retained within sleeve 230. It will be appreciated here that enclosed space 250 is formed within the housing and is occupied by an aerosol forming component within sleeve 230. FIG. 3 will be used to further describe some aspects of various embodiments described herein.

Figure 4:
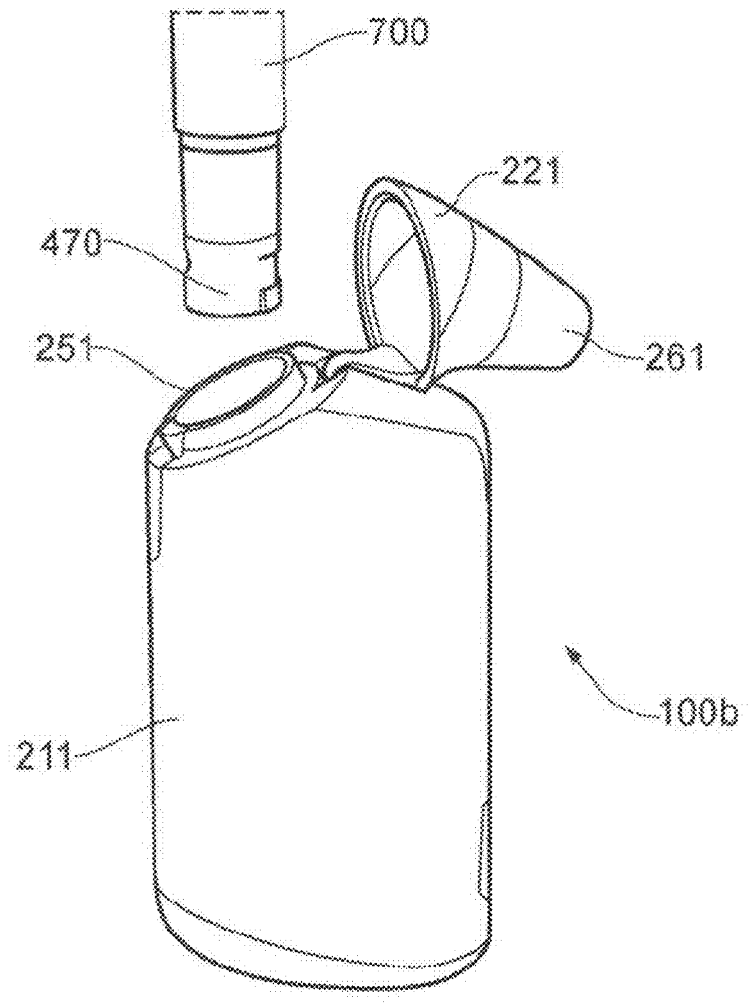
FIG. 4 is a diagram of an alternative device in accordance with another embodiment of the present disclosure.

FIG. 4 shows an alternative embodiment of the present disclosure. FIG. 4 shows device **100*b*. Similarly to device 100, device 100*b* comprises a housing formed from a chassis section 211 and a hatch section 221. Hatch section 221 is connected to chassis section 211 and is moveable between a first position wherein an enclosed space 251 is formed for an aerosol forming component to be located for aerosol generation, and a second position wherein the chassis section 211 and hatch section 221 are spaced so as to provide access to the space 251. In FIG. 4, hatch section 221 is shown in the section position providing access to space 251. According to the embodiment of FIG. 4, space 251 may define a sleeve having a generally longitudinal profile. The inner surface of the sleeve may be shaped so as to receive an aerosol forming component 700. It will be appreciated that in the embodiment of FIG. 4, the hatch section is pivotable between the first and second positions. However, said movement between the first and second positions could also be achieved via sliding, swiveling, etc. Hatch section 221 also may comprise mouthpiece section 261. In a similar fashion to device 100, mouthpiece section 261 may define an outlet which forms a fluid connection with space 251 and an air inlet (not shown) thereby allowing for air to flow through the device 100*b* such that aerosol can be entrained when an aerosol forming component is present in space 251** and activated.

Figure 7:
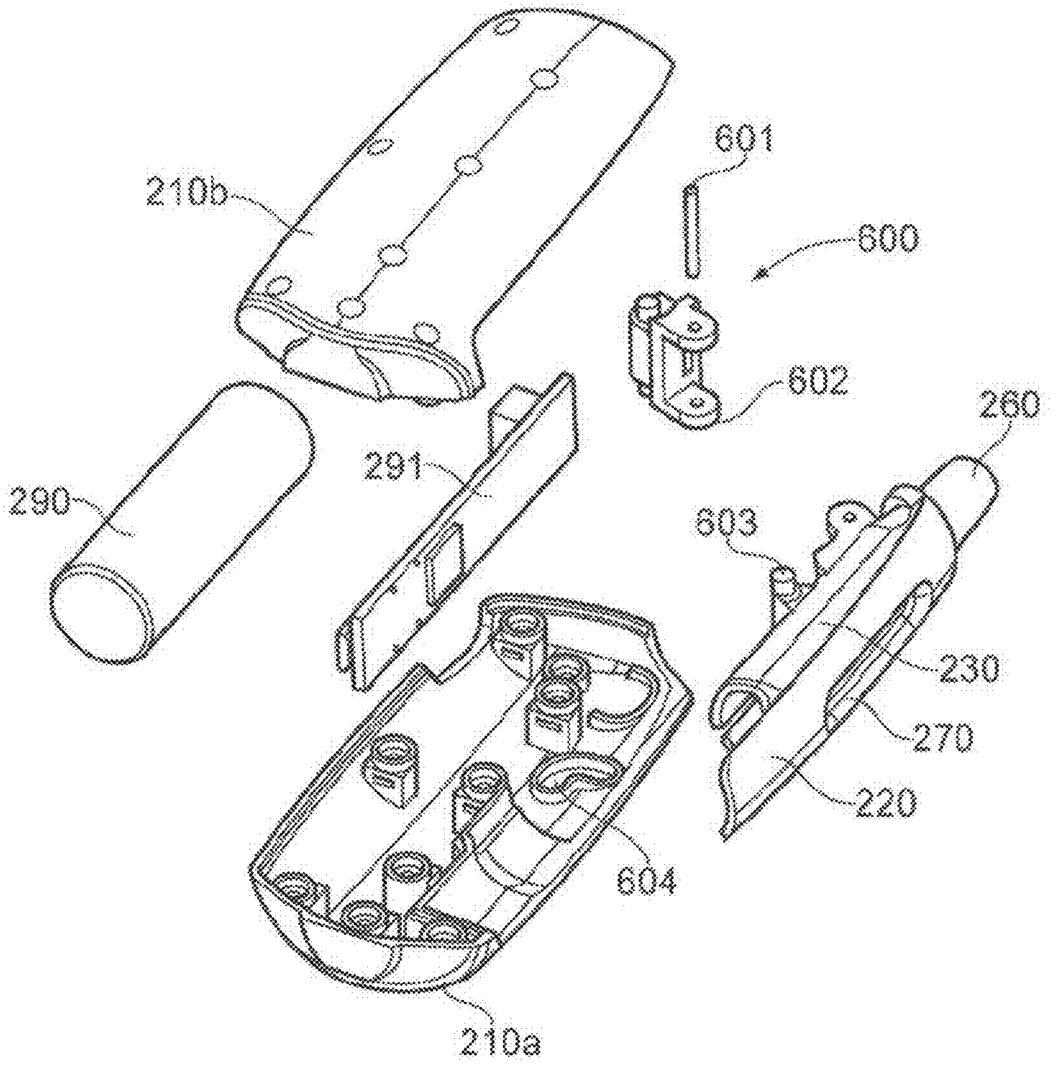
FIG. 7 is an exploded diagram showing certain components of the device of the embodiment of FIG. 2.

Turning back now to the embodiment of FIG. 2, FIG. 7 shows an exploded diagram of device 100. As will be apparent from FIG. 7, chassis sections **210*a* and 210*b* can be connected together so as to encase a power supply 290 (such as a battery, which may be rechargeable via wired or wireless means), a printed circuit board (PCB) 291 comprising various control circuitry providing for the functionality of the device, a space for receiving an aerosol forming component via the sleeve 230 of the hatch section, and a mechanism 600 connecting the chassis section 210 and the hatch section 220 and facilitating movement from the first position to the section position. As will be apparent from FIG. 7, mechanism 600 can comprise one or more parts which function to connect the chassis and hatch sections, and which facilitates their movement from the respective first to second positions. In this regard, mechanism 600 may be comprised of formations on the chassis section 210, formations on the hatch section 220 and independent (i.e. separately formed) components. In this example the control circuitry 550 is in the form of a chip, such as an application specific integrated circuit (ASIC) or microcontroller, for controlling the device 100. The circuit board 291 comprising the control circuitry may be arranged between the power supply and the space 250. The control circuitry may be provided as a single element or a number of discrete elements. The control circuitry may be connected to a pressure sensor to detect an inhalation on mouthpiece 260** and, as mentioned above, this aspect of detecting when there is airflow in the device and generating corresponding airflow detection signals may be conventional.

In one embodiment, mechanism 600 may comprise a dowel (pin) 601 and a carriage spring 602 and respective formations on the chassis section 210 and the hatch section 220. In one embodiment, dowel 601 may connect carriage spring 602 to both the hatch section 220 and the chassis section 210, thereby facilitating movement of the hatch section 220 from the first position to the section position. The carriage spring 602 may be biased against the hatch section 220 so as to urge it towards the second position. The hatch section may be retained in the first position via lug 603 being releasably positioned within the longitudinal projection of the L-shaped recess/groove 604. When lug 603 is moved to the lateral projection of the L-shaped recess/grove 604, carriage spring 602 is able to urge hatch section 220 away from the chassis section 210 and thus into a spaced position (the second position).

Figure 5A:
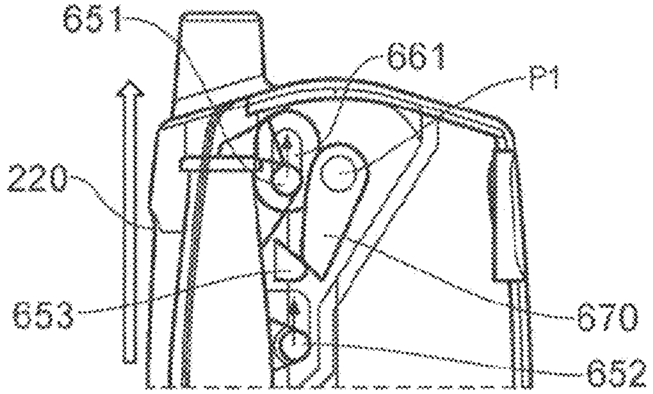
FIGS. 5*a* to 5*c* show one example of a suitable mechanism for transitioning the cover section from the first position to the second position in accordance with the embodiment of FIG. 2.
Figure 5B:
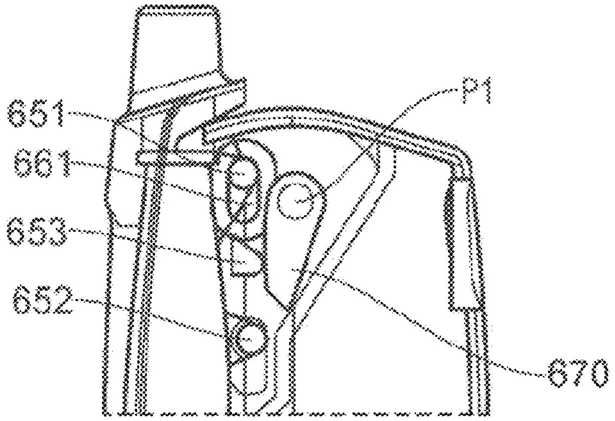
Figure 5C:
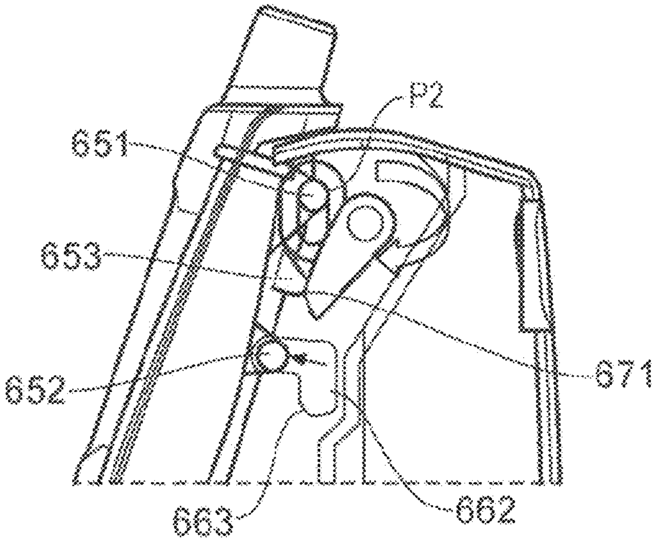

In a further embodiment, an exemplary mechanism for facilitating connection and movement between the chassis section 210 and the hatch section 220 is shown in FIGS. 5*a* to 5*c*. Mechanism 650 is shown in FIGS. 5*a* to 5*c*. Mechanism 650 comprises a first lug 651 and a second lug 652, both located on the hatch section 220. Lug 651 resides within a vertical slot 661 formed within chassis section 210 (it may be that the slot 661 is formed by opposing parts of two chassis section components 210*a* and 210*b* respectively). Slot 661 is sized and oriented so as to allow longitudinal movement of lug 651 within the slot. Lug 652 resides within a generally L-shaped slot 662 formed within chassis section 210 (again, it may be that the slot 662 is formed by opposing parts of two chassis section components 210*a* and 210*b* respectively). Mechanism 650 also comprises a biasing cam 670 which is anchored around a pivot P1. Biasing cam 670 is urged towards the hatch section 220 by a biasing spring (not shown). Biasing cam includes a retaining shoulder 671. Retaining shoulder 671 interacts with an anchoring projection 653 of the hatch section 220. Together, the components of mechanism 650 provide a simple and robust mechanism for facilitating connection and movement between the chassis section 210 and the hatch section 220. The operation of the mechanism 650 will now be described in more detail.

When the hatch section 220 is in the first position (as shown in FIG. 5*a*) lugs 651 and 652 are located in the distal most sections of their respective slots 661 and 662. Furthermore, in this position, anchoring projection 653 engages retention shoulder 671. Due to the respective orientations of the upper surface of anchoring projection 653 and the lower surface of retention shoulder 671, the urging of the biasing cam 670 towards the hatch section provides a proximally acting force on the anchoring projection 653. Furthermore, slope 663 of slot 552 generally urges the hatch section 220 (and thus the anchoring projection 653) towards the biasing cam 670 so that the tip of the anchoring projection 653 resides under the retention shoulder. Such an arrangement generally retains the hatch section 220 in the first position and provides the user with a perceptible engagement of the hatch section in the first position as the anchoring projection 653 rides over and is then retained under the retention shoulder 671.

When the user wants to move hatch section 220 towards the second position, the hatch section 220 is generally moved upwards (proximally with respect to the mouthpiece, as indicated by the arrows in FIG. 5*a*). The surface feature 270 may make such a movement easier. Such a movement results in lug 652 riding up slope 663 (since it is being biased towards the slope 663 by the biasing cam 670 and biasing spring), and then along the longitudinal projection of slot 663. Similarly, lug 651 travels proximally along slot 661. Further, anchoring projection 653 rides over retention shoulder 671. Upon continued movement of the hatch section 220, lug 652 becomes positioned at the intersection of the longitudinal and lateral portions of slot 662. At the same time, lug 651 reaches the proximal most portion of slot 661. As a result, hatch section 220 is no longer retained in the first position since lug 652 is free to move laterally in the lateral portion of L-shaped slot 662. As shown in FIG. 5*c*, under the influence of the biasing cam 670 and biasing spring (which acts against the biasing cam), the hatch section 220 is urged away from the chassis section 210 into the section position. In this regard, due to the location of lug 651 in the proximal most position of slot 661, hatch section pivots around a second pivot point P2 when moved into the second position. When the user wishes to return the hatch section 220 to the first position, the above sequence of steps is performed in reverse.

Figure 6:
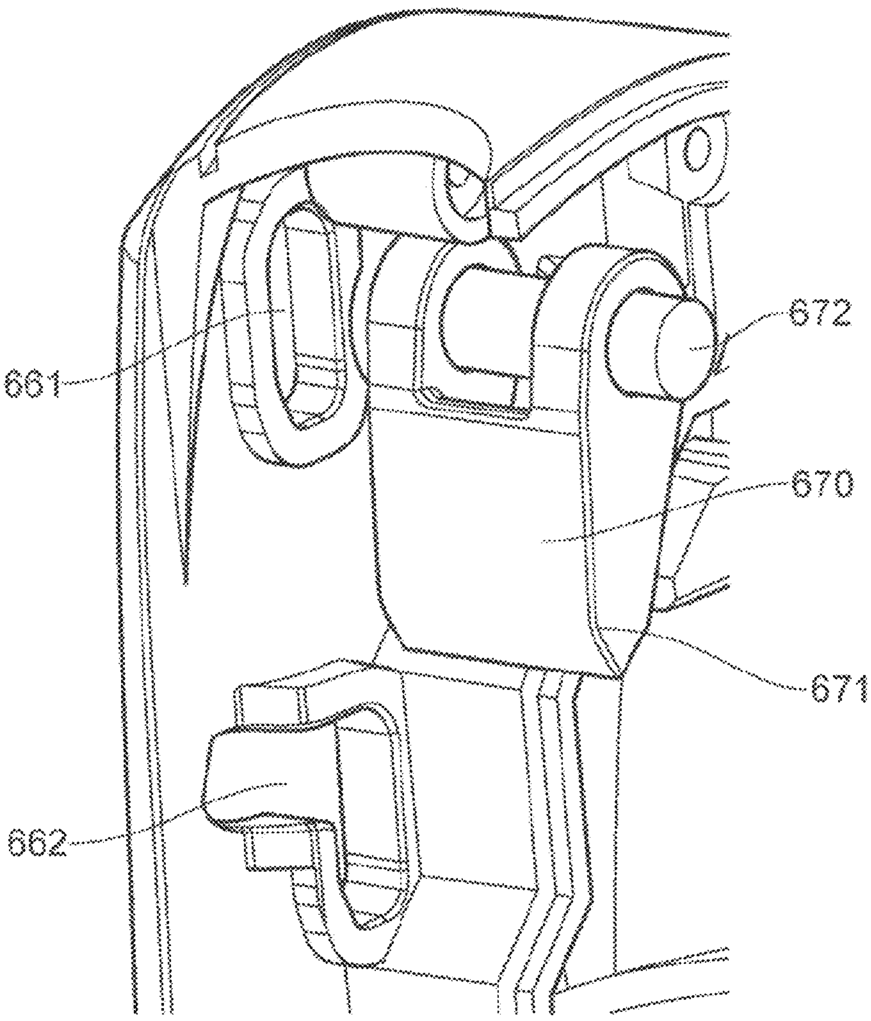
FIG. 6 is a perspective view of part of the internal mechanism shown in FIGS. 5*a* to 5*c*.

FIG. 6 provides a cut away view of through the chassis housing 210 such that part of mechanism 650 can be seen more clearly. As can be seen biasing cam 670 is mounted on rod 672 which forms pivot P1. When urged toward the hatch section 220 by a biasing spring (not shown), the biasing cam 670 can drive the hatch section 220 into the second position provided that lug 652 is in the lateral projection of slot 662.

Figure 8:
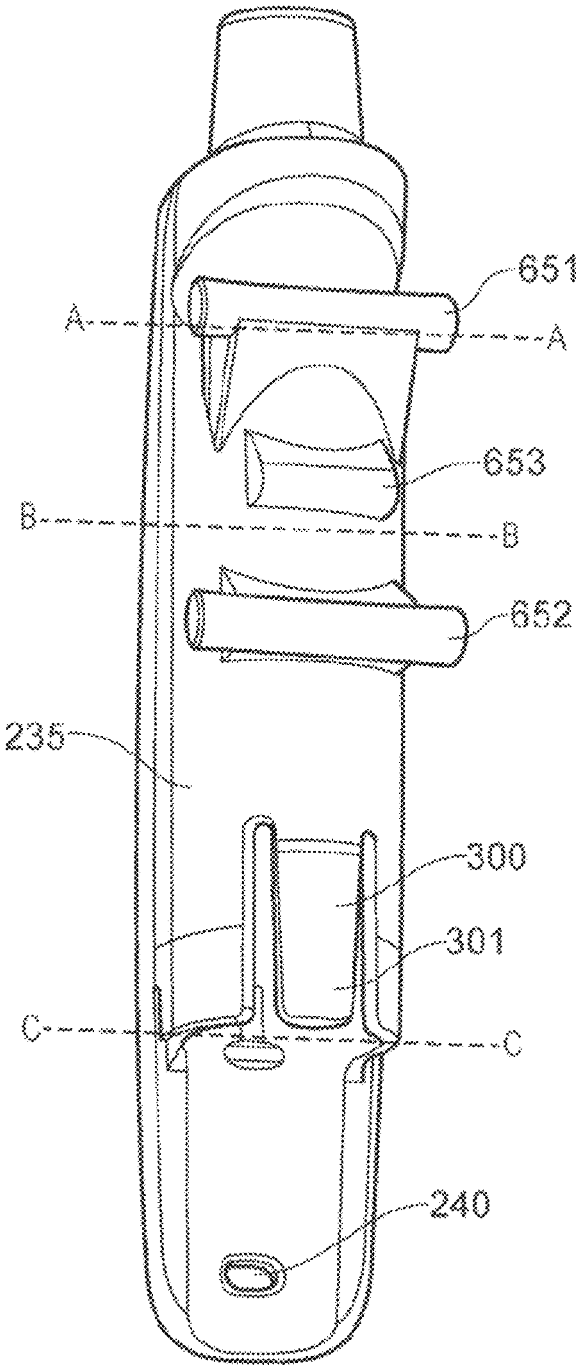
FIG. 8 is a perspective view of the hatch section and shows part of the internal mechanism shown in FIGS. 5*a* to 5*c*.

FIG. 8 shows a perspective view of hatch section 220 when detached from device 100. As can be seen, in this embodiment hatch section comprises a sleeve 235 upon which lugs 651 and 652 are mounted, as well as anchoring projection 653. FIG. 8 also illustrates an alternative position for the inlet 240. Thus, the inlet on the device can be formed in any component provided that air can enter the space 250 for accommodating the aerosol forming component. FIG. 8 also shows retention section 300 which, in this embodiment, is a flexible tang 301 which is forced outwards upon insertion of a suitable aerosol forming component in sleeve 235. Due to the general rigidity of the material used to form the tang 301, it generally resists outward deflection and as such serves to provide a degree of grip against the aerosol forming component. This then provides a force which helps to resist removal of the aerosol forming component from sleeve 235.

As described above, there is generally provided a hatch section 220 which in some embodiments comprises a sleeve 235 which is suitable for receiving an aerosol forming component. Due to the way in which the present device is used, the aerosol forming component may well be inserted into the sleeve 235 when the sleeve opening 236 is facing downwards. As a result, there is potentially a risk in some implementations that the inserted aerosol forming component may fall out of the sleeve 235 before the hatch section 220 is moved back to the first position. Accordingly, hatch section 235 may be generally provided with a retention section which is configured to resist removal of the aerosol forming component following insertion into the sleeve. This retention section could take different forms. For example, in one embodiment, the retention section is formed from a flexible tang, such as that shown in FIG. 8. Other suitable retention sections may include: a latch 302 (shown in the embodiment of FIG. 3) which engages with a corresponding recess 303 on the aerosol forming component; one or more ribs on the inside wall of the sleeve 235 which engage with the outer surface of the aerosol forming component and resist its removal; a magnet positioned at a relevant section of hatch section 220/sleeve 235 which interacts with a suitable metal component of the aerosol forming component, such as the heater, to resist removal from the sleeve 235. In a preferred embodiment, the hatch section includes a sleeve which comprises a flexible tang at an opening of the sleeve.

Figure 9A:
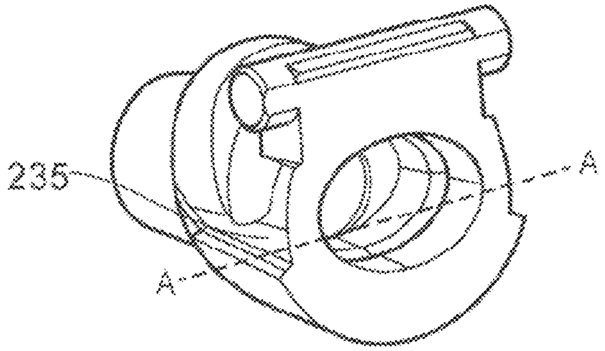
FIGS. 9*a* to 9*c* show a range of sections taken through the longitudinal axis of the sleeve of the hatch section.
Figure 9B:
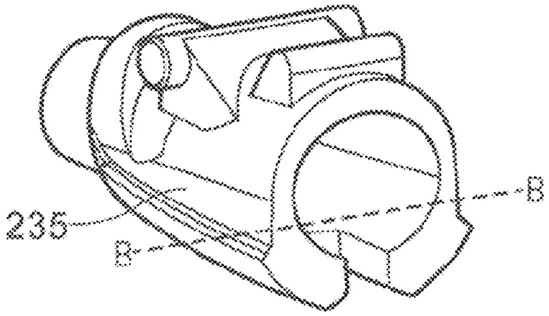
Figure 9C:
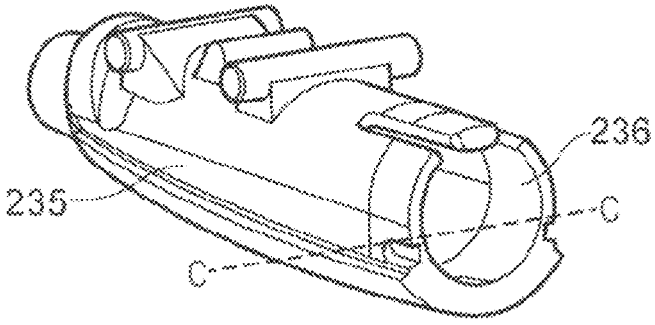
Figure 11A:
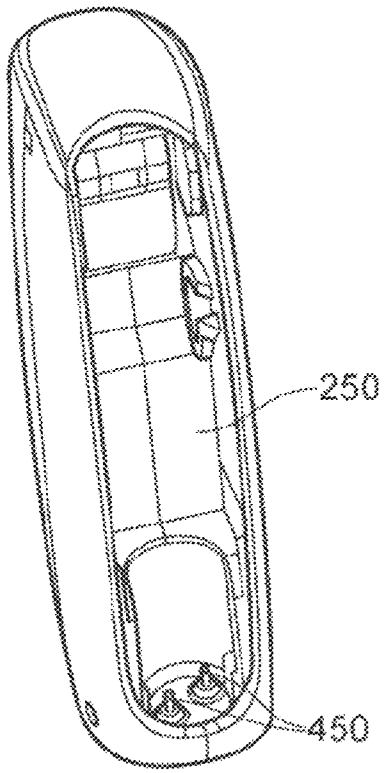
FIG. 11*a* is a perspective view showing the internal space within the housing of the device of FIG. 2.
Figure 11B:
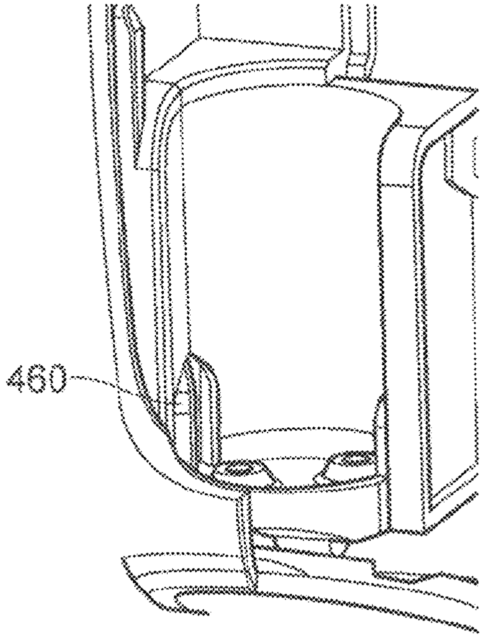
FIG. 11*b* is a closed up view of the base of the internal space within the housing of the device of FIG. 2.

Turning now to FIGS. 9*a* to 9*c*, where various cross section cut-aways along the lines A-A, B-B, C-C of FIG. 8 are shown. The cross section C-C is generally taken at the sleeve opening 236. In one embodiment, sleeve opening 236 has a generally circular cross section. However, it is possible that the sleeve opening could take another cross section. As is depicted in FIGS. 9*a* to 9*c*, sleeve 235 may have a cross-section profile that varies along its length. For example, whilst the cross-section taken at line C-C may be generally viewed as being circular, the cross section becomes progressively oval long the length of the sleeve 235. In particular, the cross-section taken at line B-B is generally more oval than the cross-section at line C-C. Further, the cross-section taken at line A-A is generally more oval than the cross-section at line B-B. Thus, the cross section of sleeve 235 varies between a first point along its length and a second point along its length. In this particular embodiment, the cross-section of sleeve 235 progressively varies so as to match the changing longitudinal cross-sectional profile of a corresponding aerosol forming component. In one embodiment, the cross-section of the sleeve progressively varies from a generally circular shape at a first position, to a generally oval shape at a second position, wherein the second position is downstream with respect to the direction of insertion of the aerosol forming component into the sleeve. In one embodiment, the chassis section 210 may also include one or more ridges or lugs 460 (or other suitable surface feature), as shown in FIG. 11*b*, which correspond to a longitudinal slot 470 on the outer surface of the distal portion of the aerosol forming component. Such a combination of lugs/longitudinal slot can assist in locking the aerosol forming component in the final rotational orientation As a result, there is provided a hatch section comprising a sleeve for receipt of an aerosol forming component, the sleeve defining a longitudinal axis and comprising first and second sections spaced along the longitudinal axis which exert different rotational biases on the aerosol forming component when inserted. The advantage of this is that should the aerosol forming component have at least one non-circular cross-section, the aerosol forming component can be inserted into the sleeve 235 in any rotational orientation and yet can be progressively oriented to a desired final rotational orientation. This may be important if, for example, the final rotational orientation of the aerosol forming component has an impact on the correct operation of the system as a whole. For example, it may be that the aerosol forming component comprises electrodes that need to be positioned in a specific rotational orientation for them to engage with corresponding electrodes on the inside of the housing 200. Alternatively, it may be that the heater of the aerosol forming component is required to be orientated in a specific rotational orientation so as to ensure correct alignment with a magnetic field for inductive heating. By utilizing a sleeve which is able to automatically align the aerosol forming component into the desired rotational orientation, regardless of the rotational orientation in which it was in when initially inserted into the sleeve opening, a more seamless experience is provided to the user. In this regard, the ability to impart different rotational biases along the length of the sleeve is not limited to the specific cross section of the sleeve. For example, it is possible that a magnet could be present at a point along the sleeve, wherein said magnet interacts with a corresponding suitable metallic feature on the aerosol forming component. Due to the relative location of the magnet and the corresponding suitable metallic feature on the aerosol forming component, the aerosol forming component can be driven to a different rotational orientation relative to the rotational orientation in which it was in when inserted into the sleeve opening.

Figure 10:
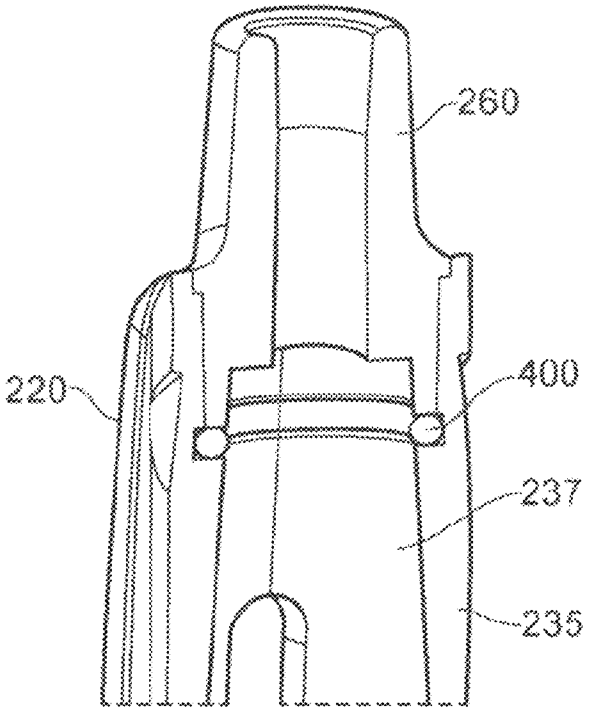
FIG. 10 is a perspective view of a sectional view parallel with a longitudinal axis of the sleeve of the hatch section.

Turning now to FIG. 10, there is shown a cross-sectional view of the hatch section 220 along a longitudinal axis of the hatch section 220. Towards the proximal most end of sleeve 235 there may be provided a seal 400, such as a sealing ring. Seal 400 functions to provide a seal between an inner surface 236 of sleeve 235 and an outer surface of the aerosol forming component when inserted into the sleeve 235. This seal serves to help ensure that when the user inhales on mouthpiece 260, airflow is drawn through the aerosol forming component, rather than along its outer perimeter.

In one embodiment, the aerosol forming component is urged into contact with the seal when the aerosol forming component is present in the sleeve and the hatch section is in the first position. In one embodiment, this may be effected by one or more biasing projections located on an inner wall of housing. In the embodiment of FIG. 11*a*, biasing projections 450 are spring loaded electrodes ("pogo pins") which serve to contact the distal most end of the aerosol forming component and urge it into further contact with seal 400. It will be appreciated that the one or more biasing projections need not be sprung electrodes, but could alternatively be a ridge or other surface feature on the inner wall of housing 100 which serves to urge the aerosol forming component into further contact with seal 400. It may be desirable to have such biasing projections as they may serve to reduce the manufacturing tolerances within which the housing must be made.

Figure 12:
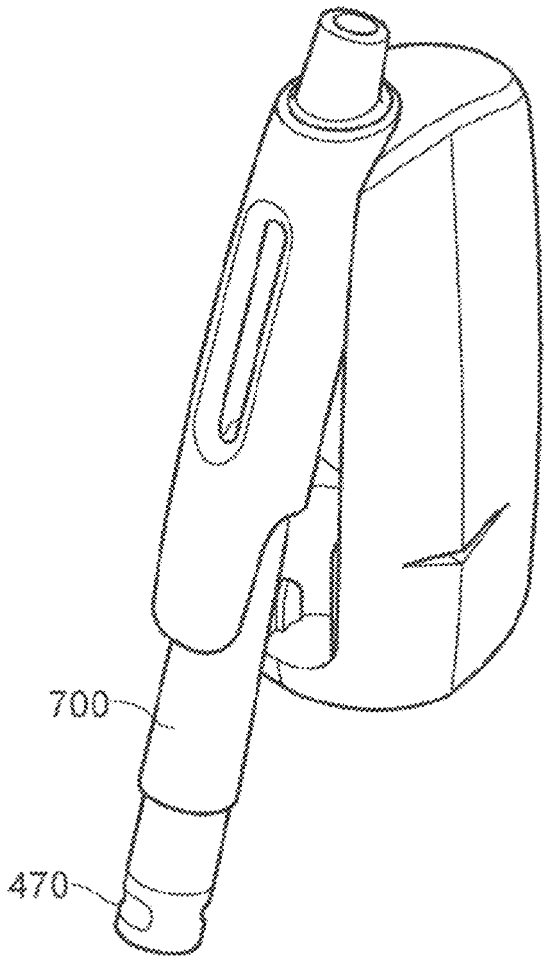
FIG. 12 provides a representational image of an aerosol forming component being inserted into the sleeve of the hatch section of the device of FIG. 2.

Whilst not a critical aspect of embodiments of the present disclosure, a suitable aerosol forming component for positioning within space 250, 251 will now be described in general. The aerosol forming component 700, such as that shown in FIG. 12, includes an aerosol generator arranged (not shown) in an air passage extending along a generally longitudinal axis of the aerosol forming component 700. The aerosol generator may comprise a resistive heating element adjacent a wicking element (liquid transport element) which is arranged to transport source liquid from a reservoir of source liquid within the aerosol forming component to the vicinity of the heating element for heating. The reservoir of source liquid in this example is adjacent to the air passage and may be implemented, for example, by providing cotton or foam soaked in source liquid. Ends of the wicking element are in contact with the source liquid in the reservoir so that the liquid is drawn along the wicking element to locations adjacent the extent of the heating element. The general configuration of the wicking element and the heating element may follow conventional techniques. For example, in some implementations the wicking element and the heating element may comprise separate elements, e.g. a metal heating wire wound around/wrapped over a cylindrical wick, the wick, for instance, consisting of a bundle, thread or yarn of glass fibers. In other implementations, the functionality of the wicking element and the heating element may be provided by a single element. That is to say, the heating element itself may provide the wicking function. Thus, in various example implementations, the heating element/wicking element may comprise one or more of: a metal composite structure, such as porous sintered metal fiber media (Bekipor® ST) from Bekaert, a metal foam structure, e.g. of the kind available from Mitsubishi Materials; a multi-layer sintered metal wire mesh, or a folded single-layer metal wire mesh, such as from Bopp; a metal braid; or glass-fiber or carbon-fiber tissue entwined with metal wires. The "metal" may be any metallic material having an appropriate electric resistivity to be used in connection/combination with a battery. The resultant electric resistance of the heating element will typically be in the range 0.5-5 Ohm. Values below 0.5 Ohm could be used but could potentially overstress the battery. The "metal" could, for example, be a NiCr alloy (e.g. NiCr8020) or a FeCrAl alloy (e.g. "Kanthal") or stainless steel (e.g. AISI 304 or AISI 316). Upon activation of the device, power may be delivered from power supply 290 to the aerosol forming member 700 via electrodes 450.

In order to address various issues and advance the art, this disclosure shows by way of illustration various embodiments in which the claimed invention(s) may be practiced. The advantages and features of the disclosure are of a representative sample of embodiments only, and are not exhaustive and/or exclusive. They are presented only to assist in understanding and to teach the claimed invention (s). It is to be understood that advantages, embodiments, examples, functions, features, structures, and/or other aspects of the disclosure are not to be considered limitations on the disclosure as defined by the claims or limitations on equivalents to the claims, and that other embodiments may be utilized and modifications may be made without departing from the scope of the claims. Various embodiments may suitably comprise, consist of, or consist essentially of, various combinations of the disclosed elements, components, features, parts, steps, means, etc. other than those specifically described herein, and it will thus be appreciated that features of the dependent claims may be combined with features of the independent claims in combinations other than those explicitly set out in the claims. The disclosure may include other inventions not presently claimed, but which may be claimed in future.

The invention claimed is:

1. An aerosol delivery system comprising:

a device, the device comprising:

a housing formed of a chassis section; and a hatch section, wherein the hatch section is connected to the chassis section and moveable between a first position, wherein the chassis section and the hatch section together define an enclosed space for an aerosol forming component to be located, and a second position wherein the chassis section and the hatch section are spaced so as to provide access to the enclosed space, and wherein the hatch section comprises a surface feature which facilitates movement of the hatch section from the first position to the second position;

a power supply, an activation means, electronics for operating the device, and an aerosol forming component.

2. The aerosol delivery system of claim 1, wherein the hatch section includes a mouthpiece including an outlet.

3. The aerosol delivery system of claim 1, wherein the hatch section comprises a surface feature which facilitates movement of the hatch section from the first position to the second position.

4. The aerosol delivery system of claim 3, wherein the surface feature is formed by a projection in an external surface of the hatch section.

5. The aerosol delivery system of claim 1, wherein the activation means is selected from one or more of a button, a touch sensor, an airflow sensor, or a pressure sensor.

* * * * *